United States Patent [19]

Lundmark

[11] Patent Number: 5,227,164
[45] Date of Patent: Jul. 13, 1993

[54] HAIR TREATMENT COMPOSITION AND METHOD

[76] Inventor: Larry D. Lundmark, 2925 84th Ave. North, Brooklyn Park, Minn. 55444

[21] Appl. No.: 743,739

[22] Filed: Aug. 12, 1991

Related U.S. Application Data

[63] Continuation of Ser. No. 471,843, Jan. 29, 1990, Pat. No. 5,041,285.

[51] Int. Cl.⁵ .............................................. A61K 7/021
[52] U.S. Cl. ...................................... 424/401; 424/65; 424/68; 424/70
[58] Field of Search ............... 424/65, 68, 70, 401; 548/105, 308, 311, 318.1; 562/569; 564/503

[56] References Cited

U.S. PATENT DOCUMENTS

| | | | |
|---|---|---|---|
| 2,761,867 | 9/1956 | Mecca | 260/299 |
| 2,898,373 | 8/1959 | Kläul | 514/629 |
| 3,230,228 | 1/1966 | Erlemann et al. | 260/295 |
| 3,275,643 | 9/1966 | Lubowe | 424/70 X |
| 3,578,656 | 5/1971 | Mecca | 260/209 |
| 3,632,596 | 1/1972 | Mecca | 260/299 |
| 3,898,243 | 8/1975 | Mecca | 260/309.5 |
| 3,927,021 | 12/1975 | Mecca | 260/309.5 |
| 3,954,989 | 5/1976 | Mecca | 424/273 |
| 3,970,756 | 7/1976 | Mecca | 424/273 |
| 4,220,166 | 9/1980 | Newell | 132/7 |
| 4,220,167 | 9/1980 | Newell | 132/7 |
| 4,296,763 | 10/1981 | Priest et al. | 132/7 |
| 4,478,853 | 10/1984 | Chaussee | 424/358 |
| 4,514,338 | 4/1985 | Hanck et al. | 260/429.9 |
| 4,602,036 | 7/1986 | Hanck et al. | 514/494 |
| 4,705,681 | 11/1987 | Maes et al. | 424/70 |

FOREIGN PATENT DOCUMENTS 1117539  2/1982  Canada .............................. 514/390

OTHER PUBLICATIONS

Panthenol in Cosmetics, Ibson Drug & Cosmetic Industry 5 pp. May 1974.
Urigacid Allantoin and Allantoin Derivatives Soap Perfumery and Cosmetics, Mecca Reprint Oct. and Nov. 1976 Issues. Parts 1 & 2 11 pp.

Primary Examiner—Thurman K. Page
Assistant Examiner—D. Colucci

[57]  ABSTRACT

A composition containing allantoin, panthenol, and a monohydric alcohol is obtained. The composition is useful for treating hair.

13 Claims, No Drawings

HAIR TREATMENT COMPOSITION AND METHOD

This application is a continuation of Ser. No. 07/471,843 filed Jan. 29, 1990 which is now U.S. Pat. No. 5,041,285 issued Aug. 20, 1991.

BACKGROUND OF THE INVENTION

1. Description of the Invention

This invention describes compositions containing organic materials which may be utilized to treat keratinous substrates such as hair.

2. Description of the Art Practices

The use of panthenol in cosmetics products is described in the article PANTHENOL IN COSMETICS, by Ibson, which appeared in DRUG & COSTMETIC INDUSTRY, May, 1974. In two articles reprinted from SOAP PERFUMERY AND COSMETICS, in the October and November, 1976 issues, there are described various allantoin containing compositions. The articles are authored by Mecca. Mecca describes various compositions including mixtures of propylene glycol and the reaction product allantoin dl panthenol.

Priest et al in U.S. Pat. No. 4296763 issued Oct. 27, 1981, describes a cap constructed of a foamed polymer which may be placed over the human scalp to aid in adding revitalizing oils to the hair. Maes in U.S. Pat. No. 4705681 issued Nov. 10, 1987, describes various hair treating compositions comprising d-panthenyl ethyl ether in mixture with d-panthenol.

U.S. Pat. No. 4220166 issued Sep. 2, 1980 to Newell describes a method for the restoring normal moisture level to hair compositions comprising various materials including cetyl alcohol and dl-panthenol. Similar disclosures to the first Newell patent are found in U.S. Pat. No. 4220167 issued Sep. 2, 1980.

Mecca in U.S. Pat. No. 3632596, issued Jan. 4, 1972, describes chlorinated aluminum compounds in combination with allantoin and propylene glycol. Mecca also discloses in U.S. Pat. No. 2761867, issued Sep. 4, 1956, the preparation of aluminum hydroxy allantionates or the corresponding chloro-hydroxy allantionates. In U.S. Pat. No. 3578656, issued May 11, 1971, Mecca describes allantion polygalacturonic acid compositions.

U.S. Pat. No. 3898243 issued Aug. 5, 1975, to Mecca describes allantoin ascorbic acid complexes. Various medicinal and cosmetic compositions containing the allantoin ascorbic acid complexes are described in this Mecca patent. In U.S. Pat. No. 3927021, issued Dec. 16, 1975, Mecca describes allantoin glycine complexes which are described as useful in medicinal and cosmetic compositions. Mecca, in U.S. Pat. No. 3954989, issued May 4, 1976, further describes allantoin ascorbic acid complexes. U.S. Pat. No. 3970756, issued Jul. 20, 1976 to Mecca also describes allantoin glycine complexes.

Hanck et al in U.S. Pat. No. 4602036, issued Jul. 22, 1986, described compositions containing aluminum panthenolate and zinc panthenolate for use as topical medicaments. Similar compositions are also described in Hanck, U.S. Pat. No. 4514338, issued Apr. 30, 1985.

U.S. Pat. No. 3230228, issued Jan. 18, 1966, to Erlemann, et al, describes various panthenol ethers and thioethers. Klaemi in U.S. Pat. No. 2898373, issued Aug. 4, 1959, describes panthenol aqueous solutions which have been stabilized for purposes of injection. U.S. Pat. No. 4478853, issued Oct. 23, 1984, to Chaussee describes a panthenol moisturizer, a polyhydric alcohol humectant and a polyether derivative.

The present invention deals with compositions which impart luster and are beneficial to keratinous substrates, such as human hair. The compositions are prepared, stabilized and utilized in such a manner as to enhance and promote the beauty of hair.

Throughout the specification and claims, percentages and ratios are by weight, temperatures are in degrees Celsius, and pressures are in KPa gauge, unless otherwise indicated. To the extent that references are cited herein, they are incorporated in their entirety by reference.

SUMMARY OF THE INVENTION

The present invention describes a substantially homogeneous product obtained by:

(A) dispersing panthenol in a monohydric alcohol at a temperature above the melting point of the panthenol to obtain a liquid melt;

(B) dispersing allantoin in the liquid melt of (A) at a temperature above the point at which the liquid melt is in the liquid phase.

A further aspect of the invention is a method of making a cosmetic composition for the treatment of keratinous substrates including the steps of preparing a substantially homogeneous product comprising (A) dispersing panthenol in a monohydric alcohol at a temperature above the melting point of the panthenol to obtain a liquid melt;

(B) dispersing allantoin in the liquid melt of (A) at a temperature above the point at which the liquid melt is in the liquid phase thereby obtaining the cosmetic product.

Yet a further aspect of the invention is a method of treating hair, including the steps of forming a product comprising:

(1) (A) dispersing panthenol in a monohydric alcohol at a temperature above the melting point of the panthenol to obtain a liquid melt;

(B) dispersing allantoin in the liquid melt of (A) at a temperature above the point at which the liquid melt is in the liquid phase to obtain the product, (2) applying the product to the hair in a sufficient amount; and (3) activating the product by heating the hair for a time and at a temperature sufficient to achieve substantive application of the product to the hair.

DETAILED DESCRIPTION OF THE INVENTION

The first aspect of the present invention to be discussed is the panthenol component. Panthenol is a naturally occurring amide corresponding to formula (I) $HOCH_2C(CH_3)_2CH(OH)C(=O)NH(CH_2)_2CH_2OH$. Panthenol is a biologically active alcohol analog of pantothenic acid. Panthenol is obtained in the dextrorotatory, levorotatory, and also as the racemic form. Panthenol of any suitable grade, and in particular, panthenol which has not been derivatized with any other functionality is exceptionally adapted to the present invention.

The second ingredient to be discussed in the present invention is allantoin. Allantoin has the structural formula shown in the incorporated references and may be described as 2,5-dioxo-4-imidazolidinyl urea or 5-ureidohydantoin. Allantoin is also referred to as glyoxydiuriede. Allantoin is a natural hydantoin occurring from purine metabolism.

Allantoin, when used in the particular invention, will usually be in the form of a complex with the panthenol. The formation of the allantoin panthenol complex is described later herein.

The third required component of the present invention is a monohydric alcohol. The monohydric alcohol is used to assist in forming a conveniently utilizable mixture of the allantoin and panthenol. It is noted at this point that while a complex of allantoin and panthenol is desirable, that such is not required and that a physical mixture of the two aforementioned ingredients may be used advantageously.

The monohydric alcohol is preferably an alcohol containing from 12 to 18 carbon atoms. Preferably the monohydric alcohol is a saturated alcohol, although an unsaturated material such as oleyl alcohol may be employed. Also preferable is that the monohydric alcohol is a primary alcohol. It is possible to use polyhydric alcohol, such as propylene glycol as a partial replacement for the desired monohydric alcohol. However, the carbon chain lengths of the typical polyhdric alcohols such as propylene glycol or glycerine are too short to be effective for all of the purposes desired in the present invention.

Particularly preferred as the monohydric alcohol is 1-tretradecanol, which is also known in the trade as myristyl alcohol.

AMOUNTS OF THE INGREDIENTS

The amount of panthenol utilized in the present invention to the monohydric alcohol is typically from about 70:30 to 30:70 weight parts. A preferred range for the aforementioned components is from 40:60 to 60:40 weight parts. Typically, the amount of the monohydric alcohol employed will be less than the panthenol in the composition.

The amount of the allantoin to the mixture of panthenol and monohydric alcohol is typically about 5:95 to about 35:65 parts. A more preferable range for the foregoing mixture of (A) and (B) is from about 10:90 to about 40:60 parts.

ADDITIONAL INGREDIENTS

The compositions of the present invention may be utilized as a 100% active composition, or may include other components typically found in compositions to treat skin or hair (keratinous substrates). For example, water, gums, kaolin, pigments such as titanium dioxide, preservatives, fragrences dyes additional emollients/conditioners, and other similarly utilized ingredients may be utilized herein.

In particular, the product described in the Summary as the homogeneous product will be blended, dispersed or dissolved in water at a respective weight ratio of from 1000:1 to 99:1, preferably from 5:95 to 1:95. The water may also be utilized with the product at a weight ratio of 65:1 to 95:1. The pH of the substantially homogeneous product described in 79 parts of water will typically be from 3 to 9.5.

METHOD OF FORMING THE PRODUCT

The homogeneous product of the invention is typically prepared as described in the Summary. The panthenol and the monohydric alcohol are mixed in the requisite proportions typically above the melting point of each of the components. Most often, the melt point of the higher melting of the two components is utilized to ensure rapid mixing. Slightly lower temperatures than the melt point may be utilized when one of the ingredients is so close to its decomposition point that the product may be denatured. Typically, the temperature for mixing the panthenol and the monohydric alcohol will be between 65° and 105° C., preferably 75° C. to 85° C. The foregoing mixture is held at the higher temperatures only long enough to obtain a workable product which is thereafter mixed with the allantoin.

Typically the allantoin and the panthenol/monohydric alcohol mixture will be combined at a temperature of about 75° C. to 105° C. Typically 80° C. to 95° C. Again, the components are held at the above temperatures only long enough to ensure that the homogeneous product is obtained.

When the homogeneous product is mixed with water and other desireable ingredients, such will typically be done within the temperature ranges previously given above.

METHOD OF APPLICATION

Typically, hair will be treated with the homogeneous product by utilizing one gram of the product per 0.2 kilogram of hair. More preferably, the product is utilized between 1.5 and 2.5 grams per 0.2 kilogram of hair.

The homogenous product is added to hair through any convenient means and in particular by using the homogeneous product as a rinse or lotion treatment for the hair.

The product is applied to the hair, which thereafter is typically treated with heat such that the hair reaches the temperature of 40° C. to 70° C. to ensure proper application of the homogeneous product to the hair. If the product is properly applied, and the hair achieves the desirable temperatures. It will be observed that the homogeneous product enters into the hair shaft without leaving a greasy feel to the hair.

Shown below are several examples of the present invention:

EXAMPLE I

A hot melt product is obtained by mixing one part of dl panthenol with one part of 1-tetradecanol.

The above ingredients are heated and mixed in a suitable reaction vessel clear and uniform. The temperature employed to obtain the clear and uniform mixture is 80° C.

EXAMPLE II

Four parts of the mixture of Example I are taken at a temperature of 80° C. and combined with one part of allantoin. The allantion is dispersed in the hot melt and the resulting product is allowed to cool, yielding an encapsulated allantoin panthenol 1-tetradecanol slurry.

EXAMPLE III

A hair conditioning complex is prepared by combining one part of the product of Example II with 79.65 parts of water, 0.3 parts of Veegum (a natural gum), 9 parts of Kaolin (a clay), 0.3 parts of titanium dioxide. A wax which is Incroquat Behenyl TMS, Polawax at 3 parts and an additional 0.75 parts of cetyl alcohol are also blended into the complex.

The foregoing components are prepared by heating the water to 50° C. and thereafter adding the Veegum, Kaolin, and titanium dioxide. The temperature of the foregoing mixture is then raised to 75° C. and the Incroquat, Polawax, and the cetyl alcohol are combined. The foregoing mixture is then stirred until a homogeneous dispersion forms and is then cooled to 30° C. during agitation. The product of Example II is then added to the foregoing base composition at 30° C. and mixing is continued until all of the components are uniformly dispersed.

EXAMPLE IV

The product is tested in the following manner:

A female subject with damaged hair is engaged to shampoo and rinse her hair in the laboratory. A quantity of the product of Example III is then applied to the wet hair fibers of the female subject immediately after hair drying.

The hair is treated with 10 grams of the composition of Example III per thousand grams of hair. The hair is then treated with heat through conventional means found in a salon. The heating step is conducted at a temperature of 50° C. for a period of 30 seconds.

The hair is observed to be easily manageable and may be combed out immediately following the treatment. Visual observation of the hair shows that the product has penetrated into the hair shaft, thereby giving a striking appearance.

These and other similar embodiments may be used with the present invention to exemplify but not limit that which is described and claimed herein.

What is claimed is:

1. A substantially homogeneous product obtained by:
   (A) dispersing panthenol in a monohydric alcohol at a temperature above the melting point of the panthenol to obtain a liquid melt;
   (B) dispersing allantoin in the liquid melt of (A) at a temperature above the point at which the liquid melt is in the liquid phase,
   wherein the monohydric alcohol contains from about 12 to about 18 carbon atoms.

2. The product of claim 1, wherein the monohydric alcohol is a saturated alcohol.

3. The product of claim 1, wherein the panthenol is present at a weight ratio to the monohydric alcohol at a 70:30 to 30:70 weight ratio.

4. The product of claim 1, wherein the temperature at which the panthenol is dispersed in the monohydric alcohol is between 65° C. and 105° C.

5. The product of claim 1, wherein the alcohol is a primary alcohol.

6. The product of claim 1, wherein the weight ratio of component (B) to component (A) is from 5:95 to 35:65.

7. The product of claim 5 wherein the alcohol is 1-tetradecanol.

8. The product of claim 1 wherein the amount of the monohydric alcohol in (A) is less than or equal to the amount of panthenol in (A).

9. The product of claim 1 wherein the panthenol reacts with the allantoin.

10. The product of claim 1 additionally comprising a member selected from the group consisting of water, gum, kaolin and titanium dioxide and mixtures thereof.

11. The product of claim 10 wherein the member is water which is present to the product in a weight ratio of from 65:1 to 95:1.

12. The product of claim 11 having a pH of from 3 to 9.5.

13. A method of making a cosmetic composition for the treatment of keratinous substrates including the steps of preparing a substantially homogeneoys product comprising
   (A) dispersing panthenol in a monohydric alcohol at a temperature above the melting point of the panthenol to obtain a liquid melt;
   (B) dispersing allantoin in the liquid melt of (A) at a temperature above the point at which the liquid melt is in the liquid phase, thereby obtaining the cosmetic product, wherein the monohydric alcohol contains from about 12 to about 18 carbon atoms.

* * * * *

UNITED STATES PATENT AND TRADEMARK OFFICE
CERTIFICATE OF CORRECTION

PATENT NO. : 5,227,164
DATED : July 13, 1993
INVENTOR(S) : Larry D. Lundmark

It is certified that error appears in the above-indentified patent and that said Letters Patent is hereby corrected as shown below:

At column 1, line 59, "described" should read "describes".
At column 3, line 23, "polyhdric", should read, "polyhydric".
At column 3, line 28, "tretradecanol", should read "tetradecanol".
At column 4, line 36, after the word, "temperatures", there should be no ".", (period).
At column 4 line 36, "It", should read "it".

In claim 4, delete the ".", (period) after the first usage of "C".
In claim 13, line 3 the word, "homogeneoys" should read, "homogeneous".
At column 1, line 15, "cosmetics", should read "cosmetic".
At column 1, line 17, "COSTMETIC", should read, "COSMETIC".
At column 1, line 43, "allantionates", should read, "allantoinates".

UNITED STATES PATENT AND TRADEMARK OFFICE
CERTIFICATE OF CORRECTION

PATENT NO. : 5,227,164
DATED : July 13, 1993
INVENTOR(S) : Larry D. Lundmark

It is certified that error appears in the above-indentified patent and that said Letters Patent is hereby corrected as shown below:

Column 1, line 44, "allantionates", should read --allantoinates--.

Signed and Sealed this

Sixteenth Day of August, 1994

Attest:

BRUCE LEHMAN

Attesting Officer    Commissioner of Patents and Trademarks